United States Patent [19]
van de Geijn et al.

[11] Patent Number: 5,526,395
[45] Date of Patent: Jun. 11, 1996

[54] SYSTEM AND METHOD FOR SIMULATING A TWO-DIMENSIONAL RADIATION INTENSITY DISTRIBUTION OF PHOTON OR ELECTRON BEAMS

[75] Inventors: Johannes van de Geijn; Huchen Xie, both of Bethesda, Md.

[73] Assignee: The United States of America as represented by the Secretary of the Department of Health and Human Services, Washington, D.C.

[21] Appl. No.: 368,589

[22] Filed: Jan. 6, 1995

[51] Int. Cl.⁶ .................................. A61N 5/10; G21K 5/00
[52] U.S. Cl. .................................................. 378/64; 378/65
[58] Field of Search ............................................ 378/64, 65

[56] References Cited

U.S. PATENT DOCUMENTS 3,487,559  1/1970  Freedman ..................... 434/218
4,868,843  9/1989  Nunan ........................... 378/152
5,418,827  5/1995  Deasy et al. .................... 378/65

Primary Examiner—David P. Porta
Assistant Examiner—David Vernon Bruce
Attorney, Agent, or Firm—Lowe, Price, LeBlanc & Becker

[57] ABSTRACT

To simulate radiation intensity distribution of a radiation beam having a field region, a penumbra region, and a scatter tail region changes in radiation intensity distribution of a reference radiation beam in the penumbra region at a reference distance from the radiation source are determined. Next, radiation intensity distribution, at the reference distance, of a radiation beam of arbitrary shape, in the field and tail regions is determined. The radiation intensity distribution of the radiation beam of arbitrary shape is simulated by superimposing the changes in radiation intensity of the reference radiation beam in the penumbra region on to the radiation intensity of the radiation beam of arbitrary shape in the field region and the tail region.

20 Claims, 8 Drawing Sheets

SYSTEM AND METHOD FOR SIMULATING A TWO-DIMENSIONAL RADIATION INTENSITY DISTRIBUTION OF PHOTON OR ELECTRON BEAMS

BACKGROUND OF INVENTION

1. Field of the Invention

This invention relates to radiation treatment planning and, more particularly, to a system and process for simulating two-dimensional radiation intensity distributions of shaped photon or electron beams which can be further used to simulate multi-dimensional radiation dose profiles to be used in developing radiation treatment plans.

2. Description of the Related Art

Computerized radiation treatment planning (CRTP) aims at user friendly, accurate, fast and versatile interactive optimization of treatment plans for individual patients. In recent years, great advances in computerized imaging technology have extended the potentially available quantitative physical and geometric patient information into the third dimension. As a result, more detailed target, i.e., body organ, tumor, etc. to be radiated, information including more detailed information about the physical composition of the target is now available. This in turn has provided a challenge for more detailed dosimetry. That is, more detailed information relating to the distribution of the radiation within the target. In order to generate detailed dosimetry information, it is necessary to first generate accurate models of the radiation distribution without consideration of target characteristics such as density etc., and then to apply the target characteristics to provide an accurate model of the dose profile within the target. In recent years, a new class of models have been developed which utilize conventional convolution techniques or superpositioning to generate accurate radiation distribution information which can be utilized in determining the dose profile within the target for radiation treatment planning purposes. Although these new models are capable of the required clinical accuracy and versatility, their operation is hindered due to the amount of convolution processing which must be performed in order to accurately simulate the radiation distribution of the radiation beam being applied prior to entering the target. Additionally, convolution processing itself requires significant processing time.

It is an object of the present invention to solve the above described problems. It is a further object of the present invention to provide a system and method for rapidly generating multi-dimensional radiation distribution profiles of photon and X-ray beams.

Additional objects, advantages and novel features of the present invention will become apparent to those skilled in the art from this disclosure, including the following detail description, as well as by practice of the invention. While the invention is described below with reference to preferred embodiments, it should be understood that the invention is not limited thereto. Those of ordinary skill in the art having access to the teachings herein will recognize additional applications, modifications and embodiments in other fields, which are within the scope of the invention as disclosed and claimed herein and with respect to which the invention could be of significant utility.

SUMMARY OF THE INVENTION

In radiation treatment planning, the objective is to develop an optimal technical application of the local radiation therapy equipment for treating the individual patient. For the present purposes, this planning process involves simulation of the physical interaction of ionizing radiation, for example using photon, such as x-ray and gamma rays, or electron beams, with the body of the individual patient. The simulation procedure involves, for any given radiation machine, the following:

a) the use of adjustable geometric beam frames i.e., representations of the beam geometry to represent the geometric aspects of the actual beams;

b) the use of a computer program to compute distributions of absorbed energy associated with any selected beam-body geometry;

c) the interactive, on-screen positioning of geometric beam frames and custom-shaping, i.e., field or on-line shaping of the beam cross sections so that the target is adequately encompassed, while avoiding adjoining structures or organs as much as possible;

d) the adjustment of relative beam contributions and cross-beam intensity distributions to satisfy cross-target dose uniformity requirements; and e) presentation of tabular and pictorial results, to serve as a basis for treatment prescription, i.e., treatment planning and execution.

The present invention concerns a novel method and system for accurately and rapidly generating two or three-dimensional cross-beam reference energy fluence distribution, or radiation intensity distribution, associated with any selected tentative or definitive geometric field shape, arising during treatment planning.

This reference distribution is the necessary basis for detailed calculation and optimization of the dose contribution from each beam, across the target volume, more or less deep inside the body.

The key element of the present invention is the generating of the energy fluence or intensity distribution on the basis of an arbitrary cross sectional geometric shape. The geometric beam shape is sharp-edged, and suggests a uniform intensity distribution inside, and zero intensity outside, while the actual radiation intensity distribution is non-uniform inside and has a penumbra, a zone with an S-shaped drop in intensity around the edge.

In essence, the transformation from the geometric field to the radiation field distribution involves a field function with a region function. Both the field function and the region function are represented by radiation source and beam-body geometry characteristic multi-dimensional matrices of numbers. The acquisition of these underlying matrices and the programmatic implementation are characteristic for this invention.

In accordance with the present invention, intensity distribution, within a target organ or tumor, of a radiation beam having a field region, a penumbra region and a tail region, known as the scattered tail region or tail for short, is simulated by first determining changes in radiation intensity of a reference radiation beam in the penumbra or edge region at a reference distance from the radiation source. Next, the radiation intensity distribution in the field region of a radiation beam having an arbitrary beam shape, at the reference distance is determined. The radiation intensity in the tail region of the radiation beam having the arbitrary beam shape is also determined. The radiation intensity distribution of the radiation beam of arbitrary shape is simulated by superimposing, using convolution or preferably a morphological operation, the changes in radiation intensity distribution of the reference radiation beam in the penumbra region on to the radiation intensity distribution of the (arbitrary shaped) radiation beam and in the tail region.

The changes in radiation intensity distribution across the beam in the penumbra region is represented as a matrix. The radiation intensity distribution of the arbitrary shaped beam in the field region and in the tail region, are represented as a second matrix. This second matrix is substantially larger than the first matrix. Simulation of the radiation intensity distribution for an arbitrary beam shape is now performed by combining the first and second matrices. To simulate a radiation dose profile within the targeted body part, characteristics such as organ or tumor density, are identified and factors, corresponding to these characteristics, are applied to the simulated radiation intensity distribution. A radiation treatment plan corresponding to the radiation dose profile can now be developed.

In accordance with the present invention, a system for simulating radiation intensity distribution of a beam characterized by field, penumbra and tail regions, includes an input device, such as a mouse, digitizer tablet, or keyboard, for identifying an arbitrary radiation beam shape. A set of radiation intensity distributions of radiation beams, with each radiation intensity distribution in the set respectively corresponding to a different arbitrary beam shape and representing a radiation distribution of the radiation beam in the field region and in the tail region at a reference distance from the radiation source, based upon beam shapes developed during a planning sesssion, are stored on a hard disc, compact disc or other electronic or magnetic storage device. Stored is a representation of changes in radiation intensity distribution of a reference radiation beam in the penumbra region for the reference beam shape at the reference distance from the radiation source. A personal computer processor, such as a Macintosh Power PC (TM), retrieves a radiation intensity distribution, from the set of stored radiation intensity distributions, corresponding to the identified arbitrary beam shape and the stored representation of changes in radiation intensity distribution of the reference beam in the penumbra region. The processor then simulates a radiation intensity distribution of the radiation beam for the identified arbitrary beam shape by superimposing the retrieved changes in radiation intensity distribution of the reference beam in the penumbra region on to the retrieved radiation intensity distribution. Beneficially, the stored representation of the changes in radiation intensity distribution of the reference beam in the penumbra region, as well as each of the stored radiation intensity distributions in the set of radiation intensity distributions, is in the form of a matrix. The processor simulates the radiation intensity distribution by combining the matrices corresponding to the changes in radiation intensity distribution of the reference beam in the penumbra region and one of the radiation intensity distributions from the set of radiation intensity distributions, using either convolutional processing or a morphological operation. The input device may also be used to identify characteristics of the target to be radiated so that the processor can simulate a radiation dose profile within the body part by applying factors, corresponding to the identified characteristics, to the simulated radiation intensity distribution. A device, such as a electronic monitor or printer, is provided and various display techniques can be utilized to display the simulated radiation intensity distribution and dose distribution in the form of a multi-dimensional model.

DESCRIPTION OF THE PREFERRED EMBODIMENT

Figure 1:
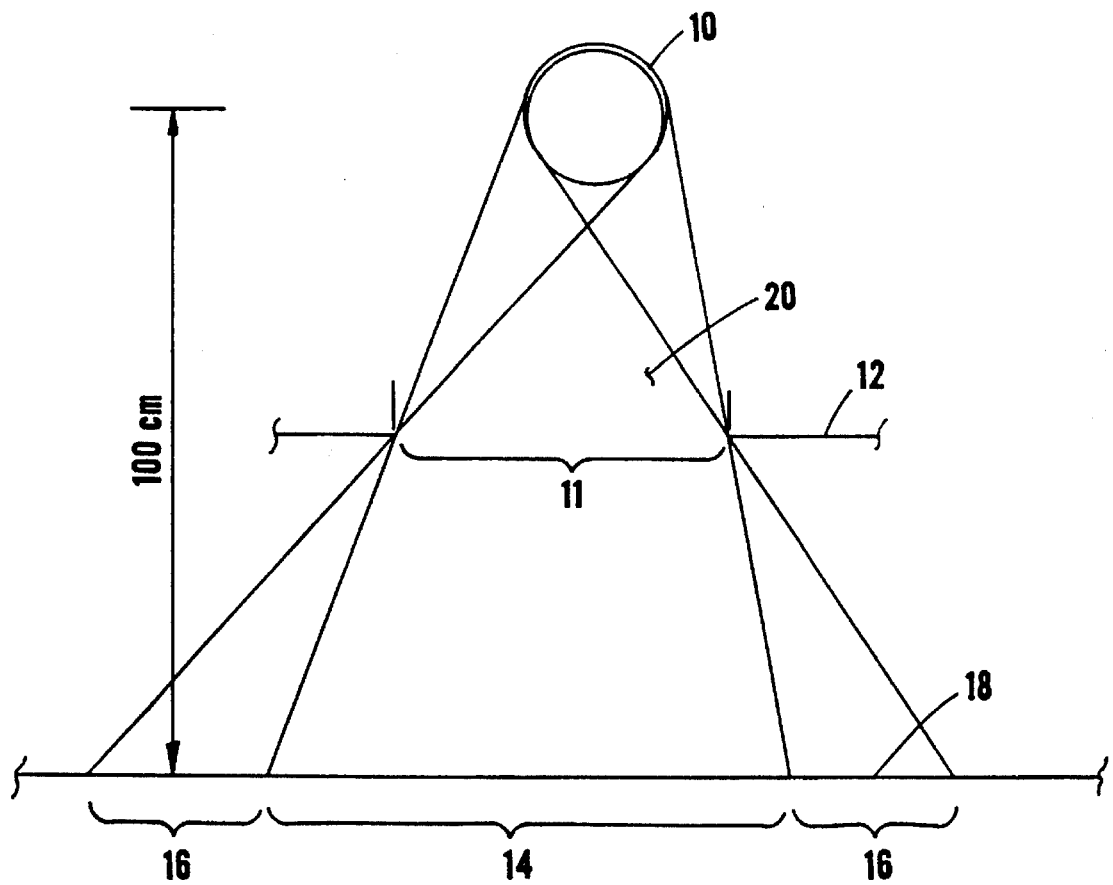
FIG. 1 depicts an exemplary photon or electron beam.

FIG. 1 depicts a radiation source 10 which emits a radiation beam 20 through a diaphragm 12. The diaphragm 12 has an opening 11 to limit the area which will be irradiated. The diaphragm may be rectangular or arbitrary shaped, i.e., custom shaped, tailored or irregularly shaped to correspond to the target to which the radiation will be applied. At a reference distance from the radiation source, typically 100 centimeters, a reference radiation beam, typically rectangular in shape, will have a field region 14 defined between identical edge or penumbra regions 16 on a plane 18 perpendicular to the direction of the beam.

Figure 2:
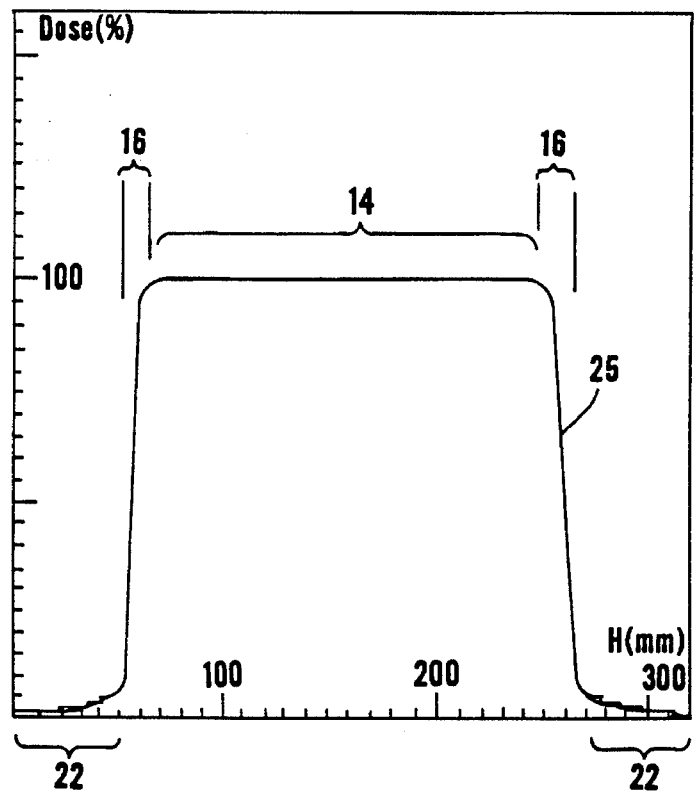
FIG. 2 depicts the radiation intensity distribution curve of the radiation beam of FIG. 1.

FIG. 2 depicts the normalized radiation distribution curve 25 across the beam along plane 18, parallel to the direction of the radiation beam. As can be seen from FIG. 2, the distribution of the radiation beam along plane 18 is non-uniform particularly at the penumbra region 16 and tail region 22.

Figure 3:
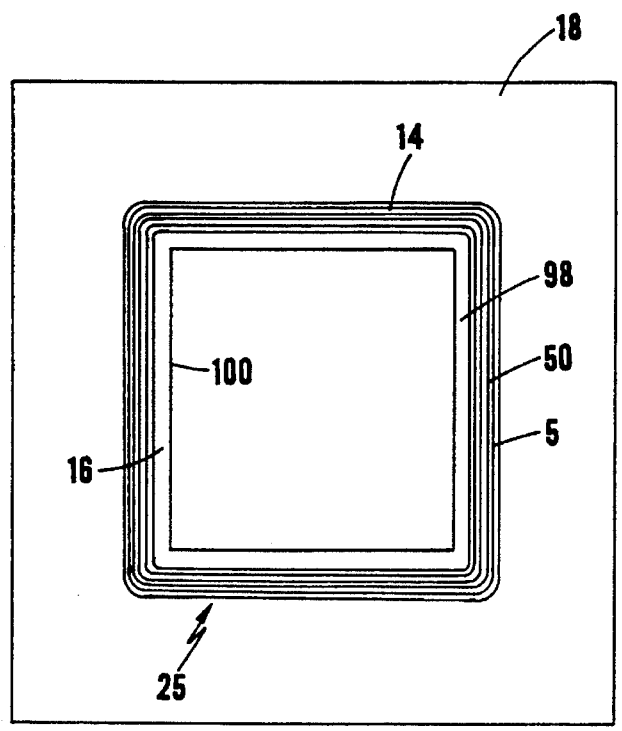
FIG. 3 depicts a two-dimensional representation of the radiation intensity distribution of the FIG. 1 beam.

FIG. 3 depicts a two-dimensional plan view at plane 18 of the normalized radiation intensity distribution curve 25 but excluding the tail region 22. The radiation intensity distribution in penumbra region 16 extends fully around the field region 14.

Figures 4, 5:
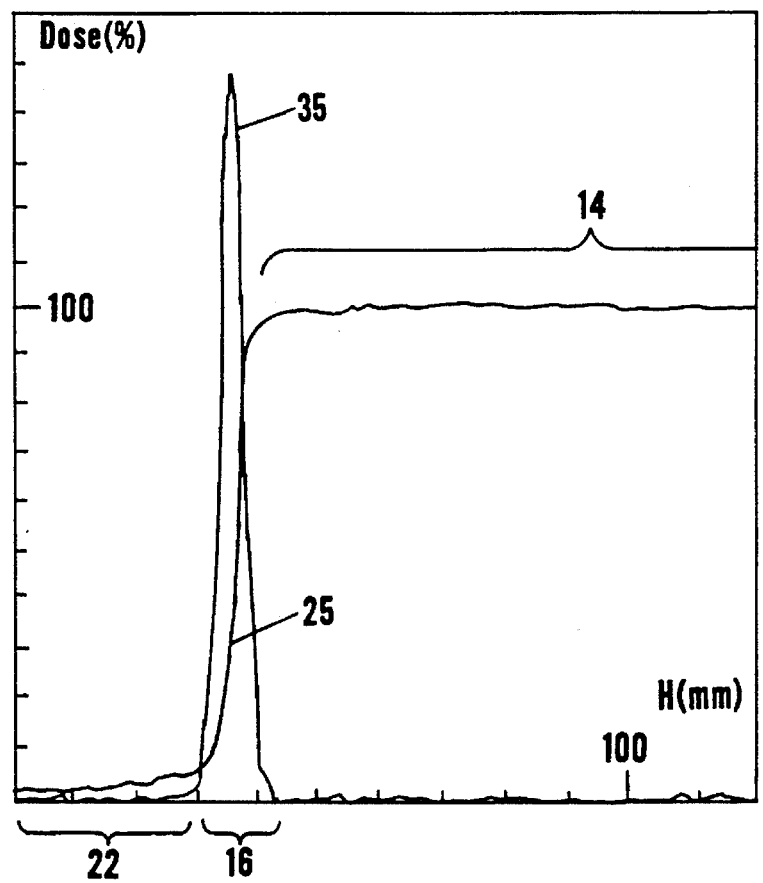
FIG. 4 depicts a change in intensity curve superimposed on a portion of the radiation intensity distribution curve shown in FIG. 2.
FIG. 5 depicts a matrix representation of the change in the radiation intensity curve of FIG. 4.

FIG. 4 depicts a portion of the radiation intensity distribution curve 25 shown in FIG. 2. Additionally, shown in FIG. 4 is curve 35 which corresponds to the change in slope of the portion of radiation intensity curve 25 which falls within the penumbra region 16.

FIG. 5 depicts a normalized matrix representation of the change in slope curve 35 shown in FIG. 4. Because the source is small, the penumbra region 16 is necessarily small. Accordingly, the size of the matrix required to represent the penumbra region is also beneficially small. As will be described in more detail below, the FIG. 5 matrix is used to generate a simulated representation of the radiation intensity distribution in a plane perpendicular to the direction of the radiation beam 20 for any arbitrary shape of the beam emitted from the radiation source 10. Because only a single small matrix representation of the penumbra region is required, for a given processing power, computation time to simulate the two-dimensional radiation intensity distributions, and hence to simulate three-dimensional dose profiles, is significantly reduced.

Referring again to FIGS. 1 and 2, the tail region 22 of the radiation intensity curve 25 in the penumbra region 16 will vary with changes in the distance between the radiation source 10 and diaphragm 12 and the diaphragm and the reference plane 18. The radiation intensity distribution in penumbra region 22 will also vary with variations in the diaphragm 12 opening. Thus, to retain a high level of accuracy while utilizing a single representation of the change in slope curve 35, these effects must be accounted for.

Figure 6:
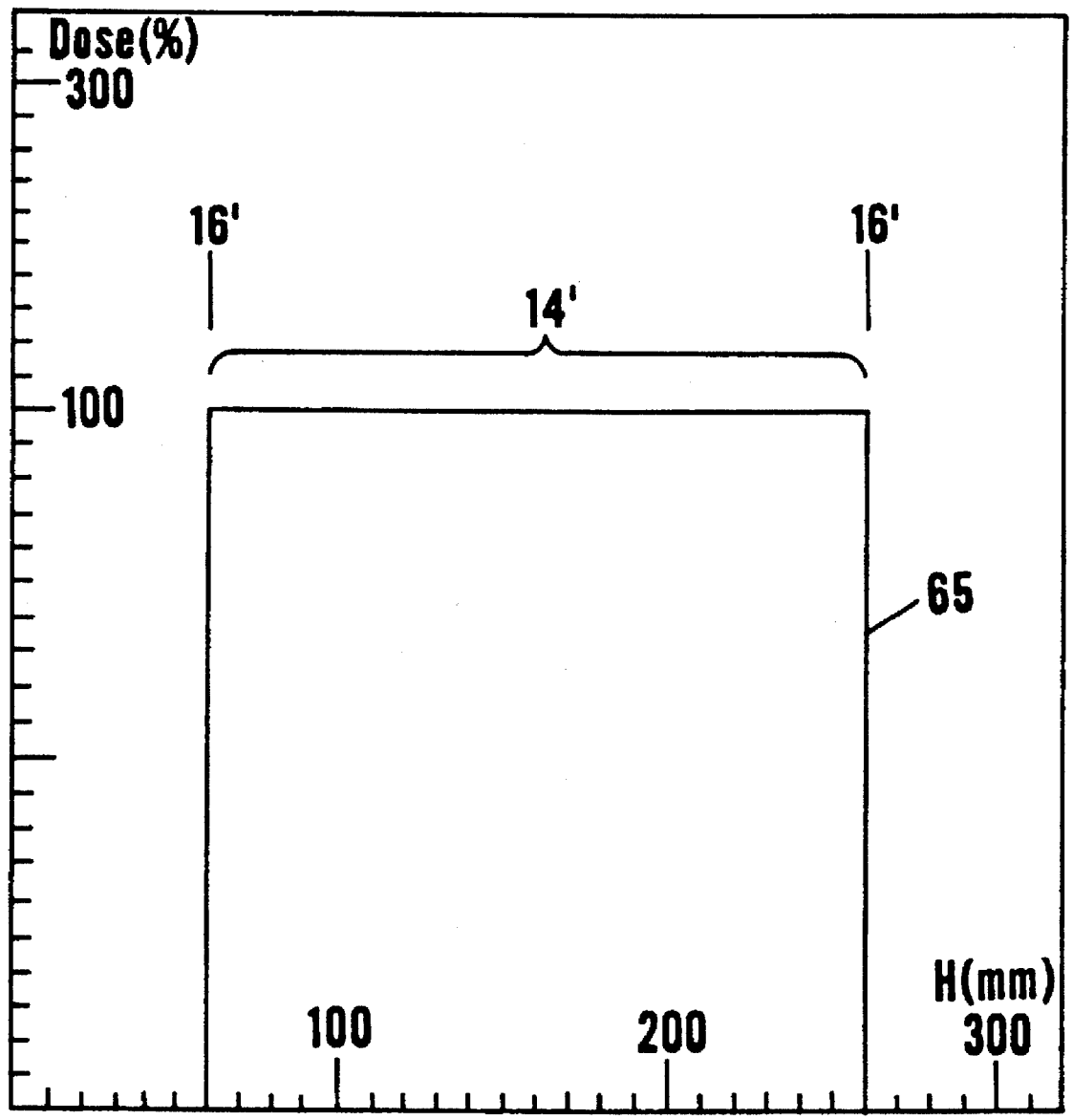
FIG. 6 depicts the radiation intensity distribution of the field region of the radiation beam of FIG. 1.

FIG. 6 depicts the graphical representation of the normalized radiation intensity distribution in the field region 14 and averaged penumbra regions 16' which are shown as vertical lines for an arbitrary shaped beam. To compensate for the difference in the tail region 22 of the reference beam and that of the arbitrary shaped beam resulting from variations in the diaphragm opening 11 and/or the distance of the radiation source 10 from diaphragm 12 or of diaphragm 12 to the plane 18, the normalized radiation intensity distribution curve 65 for the field region 14' is modified to reflect the intensity distribution in the tail region of the arbitrary beam. Accounting for the variations in the tail regions due to field size variation differences is based upon suitable empirical measurements in a small number of reference fields.

Figures 7, 8:
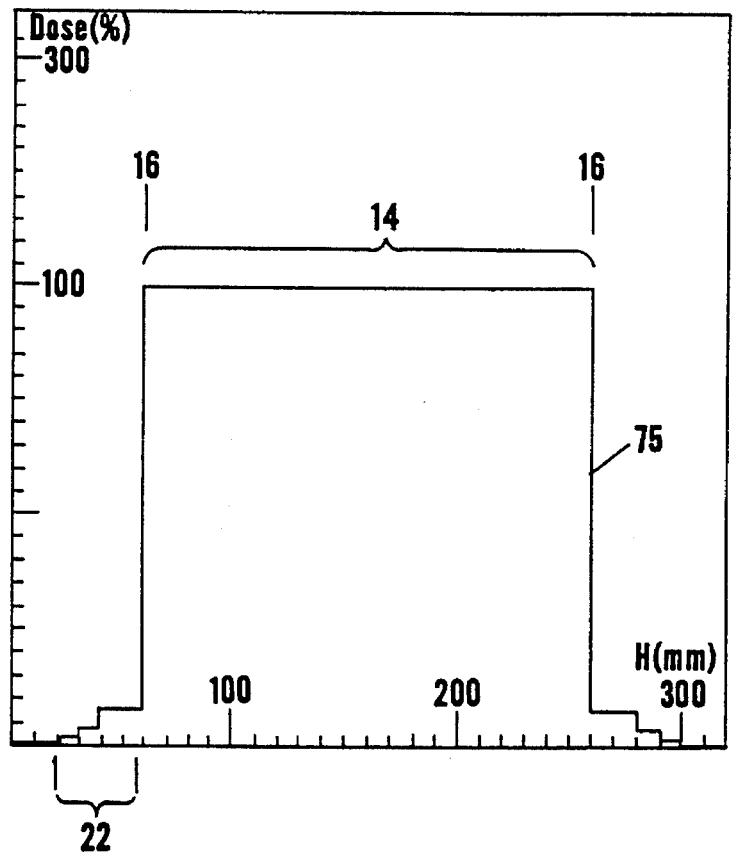
FIG. 7 depicts a partial radiation intensity distribution curve for the radiation beam of FIG. 1 corresponding to a particular radiation beam shape.
FIG. 8 depicts a matrix representation of the radiation distribution curve of FIG. 7.

The modified curve 75 is shown in FIG. 7. As noted above, the matrix of FIG. 5 represents the change in slope of the radiation intensity distribution curve for a reference beam shape at a distance of 100 centimeters from the light source 10 of FIG. 1. The 100 centimeter dimension has been selected so that plane 18 coincides with the axis of rotation of the gantry which supports the radiation source. In actuality, the targeted organ or tumor will typically require an arbitrary shaped beam for appropriate treatment. Thus, simulated radiation intensity distributions are required for different arbitrary shaped beams so that accurate profiles of the dosage of the photon or electron beams within the targeted organ or tumor can be simulated.

FIG. 8 is a matrix representation of the radiation intensity distribution curve 75 shown in FIG. 7. The matrix required to represent the field region 14 is typically large in comparison to the matrix required to define the change in slope curve 35 of FIG. 4. Therefore, the inclusion in curve 75 of FIG. 7 of the radiation intensity distribution in the tail portion for the arbitrary beam does not significantly increase the size of the matrix required to represent curve 65. It should be understood that the matrices shown in FIGS. 5 and 8 are exemplary and that the matrix representations of curve 35 of FIG. 4 and curve 75 of FIG. 7 are derived in the conventional manner which will be well understood by those skilled in the art.

Utilizing the FIG. 5 matrix and the FIG. 8 matrix, the radiation intensity distribution of the arbitrary shaped beam can now be simulated at the reference plane perpendicular to the radiation beam. Thus, two-dimensional radiation intensity distributions can be simulated and thereafter used to generate multi-dimensional dose profiles of photon or electron beams penetrating a targeted organ or tumor.

The combination or superpositioning of the FIG. 5 matrix on the FIG. 8 matrix can be performed using conventional convolution techniques. Alternatively, to significantly enhance the speed of processing, a morphological operation such as dilation, erosion, closing or opening, all of which will be well understood by those skilled in the art, can be utilized to further enhance performance.

Figure 9:
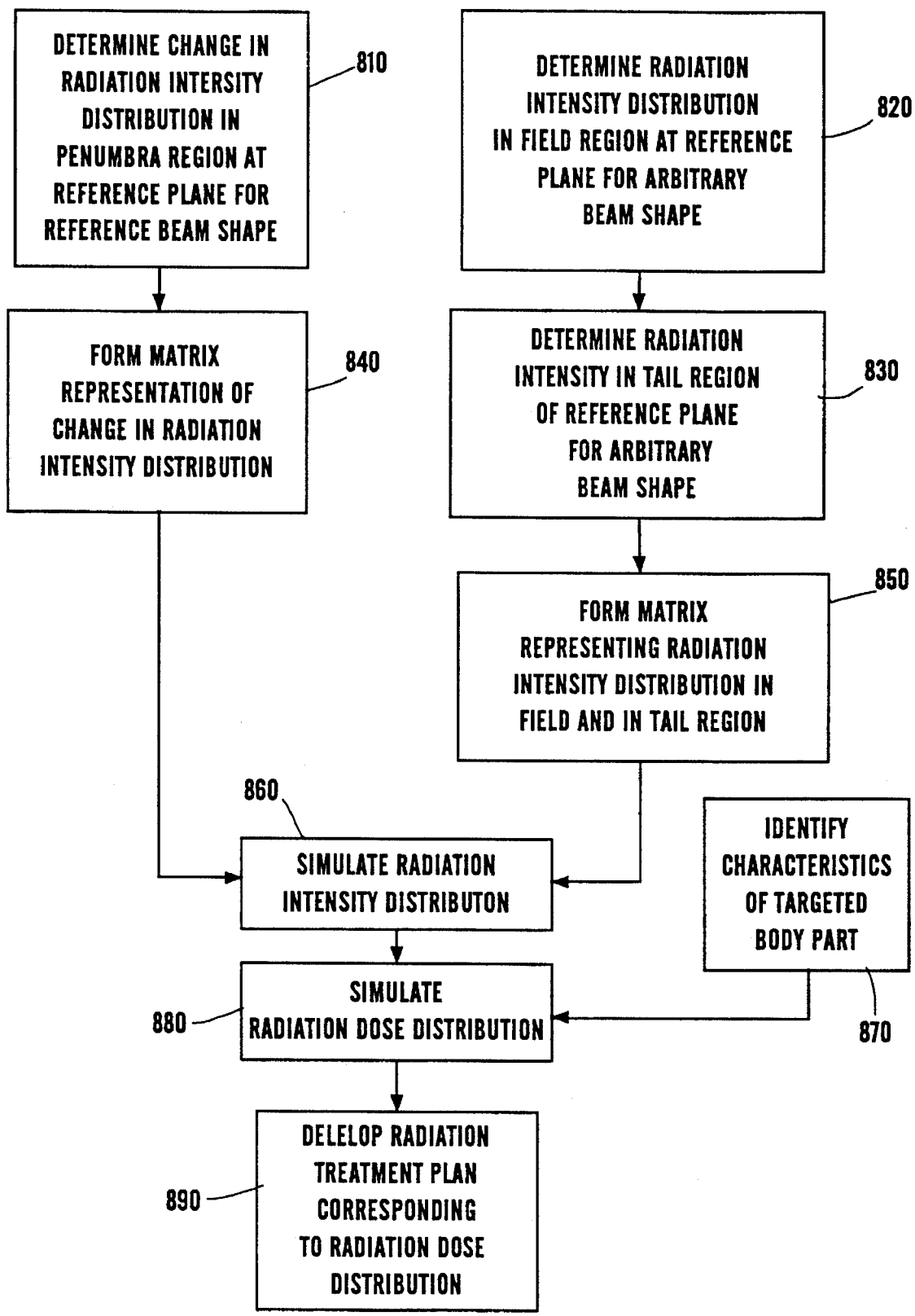
FIG. 9 is a flowchart of the steps required for simulating multi-dimensional radiation intensity distributions of photon or electron beams in accordance with the present invention.

FIG. 9 is a flowchart of the steps performed in simulating radiation intensity distribution and radiation dose profiles of photon and electron beams within a targeted organ or tumor or other body parts. In step 810, the change in the radiation intensity, i.e., the change in the slope of the normalized radiation intensity curve 25, in the penumbra area 16 for a reference beam is determined at a reference plane 18. These data form the basis of the first of the two above-mentioned essential matrices. In step 820, the radiation intensity of an arbitrary shaped beam in the field region at the reference plane is determined. Next, the radiation intensity distribution of the beam in the tail region at the reference plane is determined in step 830. In step 840, a matrix representation of the change in radiation intensity is formed. In step 850, a matrix corresponding to the field region intensity distribution of the arbitrary shaped beam and the radiation intensity distributions in the tail regions of the arbitrary shaped beam at the reference plane is formed. In step 860, the radiation intensity distribution for the arbitrary shaped beam is simulated in two-dimensions by superimposing the matrix representing the change in radiation intensity in the penumbra area for the reference beam and the matrix representing the intensity distribution in the field region and the radiation intensity distribution in the tail regions at the arbitrary shaped beam. The super-positioning may be performed using convolutional processing or a morphological operation. In step 870, characteristics of the targeted body part are identified. In step 880, the characteristics identified in step 870 or factors corresponding thereto, are applied to the simulated radiation intensity distribution generated in step 860 to simulate a radiation dose profile. In step 890, a radiation treatment plan is developed corresponding to the simulated radiation intensity distribution.

In practice the change in radiation intensity distribution the penumbra area at the reference plane as well as the determination of the radiation intensity distribution in the field region and the difference in the radiation intensity in the tail regions will be generated and stored so that they are available for use when required.

Figure 10:
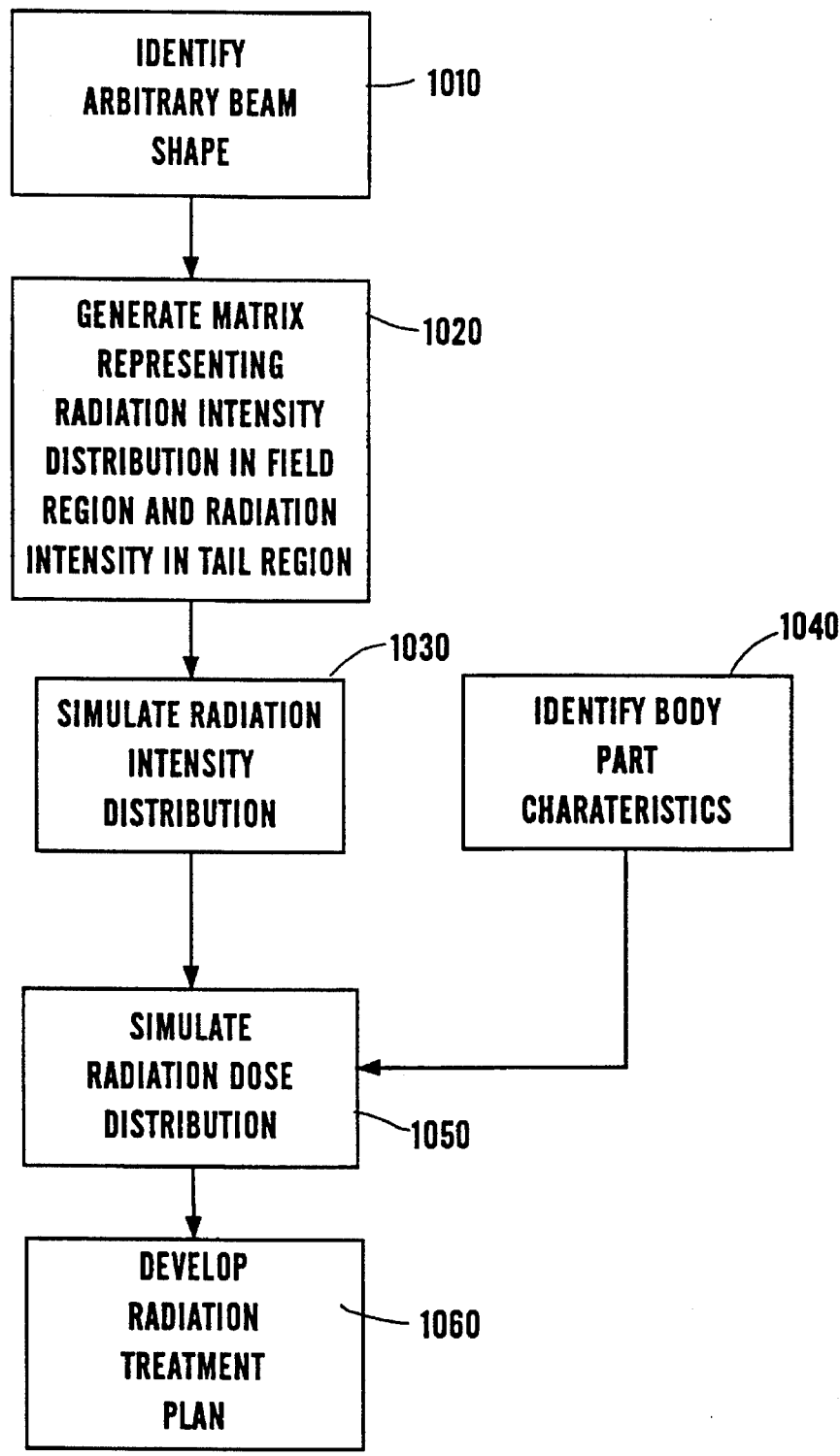
FIG. 10 is a flowchart of the steps required for simulating multi-dimensional radiation intensity distributions of photon or electron beams in a second implementation of the present invention.

FIG. 10 describes a further implementation of the present invention wherein simulations are performed utilizing the stored representation of the change in radiation intensity distribution in the penumbra region for a reference beam at the reference plane and selected representations from a set of stored representations of the radiation intensity distribution in the field region and difference in radiation intensity distribution in the tail region(s) for arbitrary beam shaped. As shown in FIG. 10, in step 1010, the arbitrary beam shape is identified in step 1010. The arbitrary beam shape will typically correspond to the target silhouette, as seen from the radiation source position. In step 1020, a representation of the radiation intensity distribution in the field region and the difference in the radiation intensity distribution in the tail region for the arbitrary beam shape as compared to the reference beam shape is selected. In step 1030, a matrix representation of the change in radiation intensity in the penumbra region is superimposed on the matrix selected in step 1020, to simulate the radiation intensity distribution for the identified arbitrary beam shape. In step 1040, characteristics of the body part which are to be radiated are identified and entered. As described above, such characteristics will include the density of the organ or tumor etc. The radiation dose profile within the body part which will be radiated can now be simulated in the conventional manner in step 1050 by applying the body part characteristics identified in step 1040 to the simulated radiation intensity distribution generated in step 1030. Finally, in step 1060, a radiation treatment plan is developed in an interactive process to simulate radiation dose distribution desired by the radiation oncologist.

Figure 11:
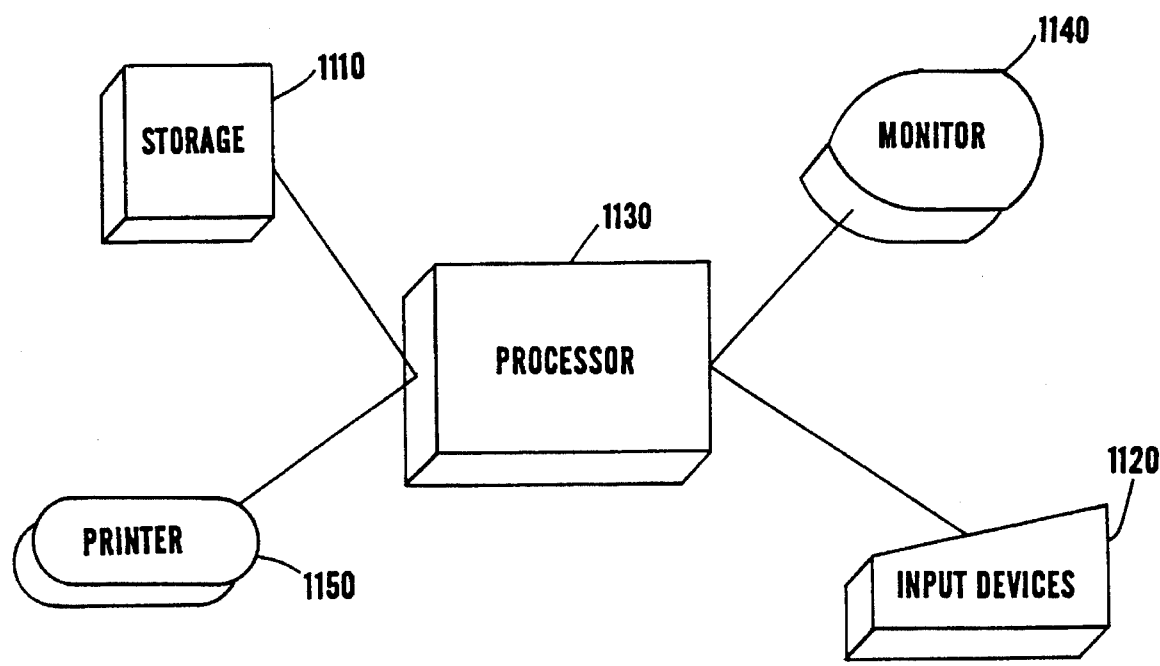
FIG. 11 is a representation of an exemplary system implementation of the present invention.

FIG. 11 depicts a system for simulating radiation dose profiles in accordance with the present invention. As shown, a matrix representation of the change in radiation intensity distribution for a reference beam at a reference plane as well as matrix representations of the radiation intensity distribution in a field region and in the tail region for an arbitrary beam shape corresponding to various arbitrary beam shapes, are stored in the storage device 1110. A keyboard or other data entry device 1120 is used to input a selected arbitrary beam shape for which a simulated multi-dimensional radiation dose profile is desired. As discussed above, the arbitrary beam shape will normally correspond to the target body part to be radiated. The input data is transmitted to the processor 1130 and responsive thereto the processor retrieves the matrix representation of the change in radiation intensity in the penumbra region for the reference beam as well one matrix from the set of matrices which represent(s) the radiation intensity distribution in the field region and in the tail region for the identified arbitrary beam shape. The processor is beneficially a personal computer processor such as a Macintosh Power PC (TM). The processor then simulates the radiation intensity distribution for the arbitrary beam shape by superimposing the two matrices using either convolution processing or a morphological operation. As discussed above, a morphological operation will simplify and speed the processing operations. The simulated radiation intensity distribution can now be displayed electronically on the monitor 1140 or may be provided in a hard copy form over printer 1150. The input device 1120 can also be used to perform target characterization. The identified body part characteristics are then applied in a conventional manner by processor 1130 to the simulated radiation intensity distribution to simulate a radiation dose distribution. Signals corresponding to the radiation dose distribution are now transferred to the display 1140 and printer 1150 for viewing by the medical professional who is responsible for developing the radiation treatment plan.

As described above, the present invention provides a system and method for rapidly simulating a custom tailored two-dimensional radiation intensity distribution of photon and electron beams. The simulated radiation intensity distributions can then be utilized in computing and displaying relative radiation dose distributions throughout a target volume as a basis for a radiation treatment plan, and ultimately the treatment prescription and delivery.

What is claimed:

1. A process for simulating radiation intensity distribution for a radiation beam having a field, penumbra and tail region, comprising the steps of:

determining changes in radiation intensity distribution of a reference radiation beam in a penumbra region at a reference distance from a radiation source;

determining radiation intensity distribution of a radiation beam of arbitrary shape in a field region at the reference distance from the radiation source;

determining radiation intensity distribution of the radiation beam of arbitrary shape in a tail region at said reference distance; and simulating a radiation intensity distribution of said radiation beam of arbitrary shape at said reference distance by superimposing said changes in radiation intensity distribution of the reference radiation beam on to said radiation intensity distribution of the radiation beam of arbitrary shape in the field region and the tail region.

2. A process according to claim 1, further comprising the steps of:

representing said changes in radiation intensity distribution of the reference radiation beam as a first matrix; and representing said radiation intensity of the radiation beam of arbitrary shape in the field region and in the tail region as a second matrix;

wherein, said simulating step includes combining said first matrix and said second matrix.

3. A process according to claim 2, wherein said step of combining said first matrix and said second matrix includes convolutional processing.

4. A process according to claim 2, wherein said step of combining said first matrix and said second matrix includes a morphological operation.

5. A process according to claim 2, wherein said first matrix is small in comparison to said second matrix.

6. A process according to claim 1, further comprising the steps of:

identifying characteristics of body parts; and simulating a radiation dose distribution within said body parts by applying factors corresponding to said identified characteristics to the simulated radiation intensity distribution.

7. A process according to claim 6, further comprising the step of developing a radiation treatment plan corresponding to said radiation dose distribution.

8. A process according to claim 1, wherein said simulated radiation intensity distribution is in the form of a two dimensional model.

9. A process according to claim 1, wherein said simulated radiation intensity distribution is in the form of a multi-dimensional model.

10. A process for simulating radiation intensity distribution of a radiation beam having a field region, a penumbra region, and a tail region comprising the steps of:

identifying a radiation beam of arbitrary shape;

generating a radiation intensity distribution in a field region and a tail region corresponding to the identified radiation beam;

simulating a radiation intensity distribution of said identified radiation beam by superimposing changes in radiation intensity distribution in the penumbra region of a reference radiation beam at a reference distance from a radiation source on to said generated radiation intensity distribution.

11. A process according to claim 10, further comprising the steps of:

representing said changes in radiation intensity distribution in the penumbra region as a first matrix; and representing said selected radiation intensity distribution of the identified radiation beam as a second matrix;

wherein, said simulating step includes combining said first matrix to said second matrix.

12. A process according to claim 11, wherein said step of combining said first matrix and said second matrix includes convolutional processing or a morphological operation.

13. A process according to claim 11, further comprising the steps of:

identifying characteristics of said body part; and simulating a radiation dose profile within said body part by applying factors corresponding to said identified characteristics to the simulated radiation intensity distribution.

14. A process according to claim 13, further comprising the step of developing a radiation treatment plan corresponding to said radiation dose profile.

15. A process according to claim 11, wherein said simulated radiation intensity distribution is in the form of a multi-dimensional model.

16. A system for simulating radiation intensity distribution of a radiation beam having a field region, a penumbra region and a tail region, comprising:

means for identifying a radiation beam having an arbitrary shape;

means for storing (i) a set of radiation intensity distributions of radiation beams, wherein each radiation intensity distribution in said set respectively corresponds to a different arbitrary shape and represents a radiation intensity distribution in a field region and in a tail region and (ii) a representation of changes in radiation intensity distribution in a penumbra region of a reference radiation beam at a reference distance from a radiation source; and processing means for (i) retrieving from said storage means a radiation intensity distribution from said set of radiation intensity distributions corresponding to the identified radiation beam and the representation of changes in radiation intensity distribution of the reference radiation beam and (ii) simulating a radiation intensity distribution of said identified radiation beam by superimposing the retrieved changes in radiation intensity distribution of the reference radiation beam on to said retrieved radiation intensity distribution.

17. A system according to claim 16, wherein:

said stored representation of the changes in radiation intensity distribution of the radiation beam is a matrix;

each of said stored radiation intensity distributions in said set of radiation intensity distributions is a matrix; and said simulating step includes combining matrices corresponding to the changes in radiation intensity distribution of the reference radiation beam and said retrieved radiation intensity distribution.

18. A system according to claim 17, wherein said processing means simulates said radiation intensity distribution by convolutional processing or a morphological operation.

19. A system according to claim 16, wherein:

said means for identifying is adapted to identify characteristics of said body part; and said processing means is adapted to simulate a radiation dose profile within said body part by applying factors corresponding to said identified characteristics to the simulated radiation intensity distribution.

20. A system according to claim 16, further comprising:

display means for displaying the simulated radiation intensity distribution;

wherein said simulated radiation intensity distribution is in the form of a multi-dimensional model.

* * * * *